(12) United States Patent
Matoba

(10) Patent No.: US 7,634,053 B2
(45) Date of Patent: Dec. 15, 2009

(54) FLUORESCENT X-RAY ANALYSIS APPARATUS

(75) Inventor: Yoshiki Matoba, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 74 days.

(21) Appl. No.: 11/708,789

(22) Filed: Feb. 20, 2007

(65) Prior Publication Data

US 2007/0211852 A1     Sep. 13, 2007

(30) Foreign Application Priority Data

Feb. 24, 2006   (JP)   ............................. 2006-047945

(51) Int. Cl.
*G01N 23/223*   (2006.01)
(52) U.S. Cl. .......................................... 378/44; 378/47
(58) Field of Classification Search .................... 378/44, 378/45, 47, 50
See application file for complete search history.

(56) References Cited

U.S. PATENT DOCUMENTS

| | | | | |
|---|---|---|---|---|
| 4,587,666 A * | 5/1986 | Torrisi et al. | .................... | 378/45 |
| 4,720,842 A * | 1/1988 | Kira et al. | ...................... | 378/45 |
| 6,266,390 B1 * | 7/2001 | Sommer et al. | ................ | 378/45 |
| 6,700,951 B2 * | 3/2004 | Sumii | ........................... | 378/44 |
| 2004/0141585 A1 * | 7/2004 | Proctor | ........................ | 378/88 |

FOREIGN PATENT DOCUMENTS

JP   2004-150990   5/2004

* cited by examiner

*Primary Examiner*—Chih-Cheng G Kao
(74) *Attorney, Agent, or Firm*—Brinks Hofer Gilson & Lione

(57) ABSTRACT

There is provided a fluorescent X-ray analysis apparatus in which a detection lower limit is improved, and it is possible to quantify a trace aimed element having been contained not only in a sample whose main component is a heavy element but also in a sample whose main component is a light element. The fluorescent X-ray analysis apparatus possesses a sample base supporting the sample, an X-ray source irradiating a primary X-ray with a predetermined irradiation position being made a center, and a detector disposed toward the irradiation position and detecting a fluorescent X-ray generated from the sample. The sample base has a detachable sample holding tool fixing the sample while being approached to the X-ray source and the detector, and a measurement is possible by selectively disposing the sample in any one of a 1st inspection position in which an irradiated face is coincided with the irradiation position, or a 2nd inspection position in which the sample is fixed to the sample holding tool, an irradiated face is approached to the X-ray source, and an inspected face is approached to the detector.

11 Claims, 7 Drawing Sheets

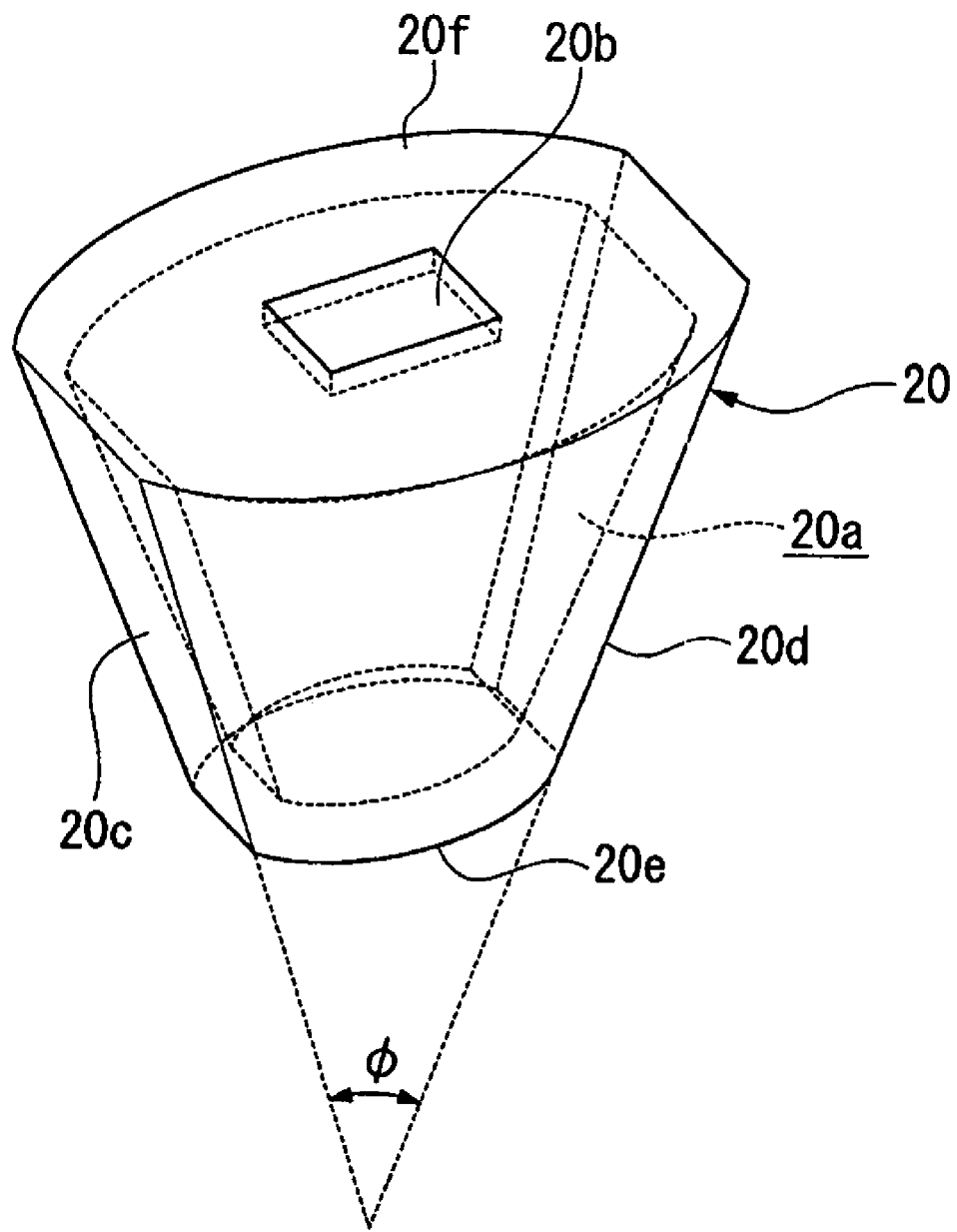
F I G. 7

FLUORESCENT X-RAY ANALYSIS APPARATUS

This application claims priority under 35 U.S.C. §119 to Japanese Patent Application No. JP2006-047945 filed Feb. 24, 2006, the entire content of which is hereby incorporated by reference.

BACKGROUND OF THE INVENTION

1. Field of the Invention

The present invention relates to a fluorescent X-ray analysis apparatus which performs an element analysis and a composition analysis of a sample by irradiating a primary X-ray to the sample and detecting a fluorescent X-ray generated from the sample.

2. Description of the Related Art

In recent years, a cadmium pollution of a food, and the like become a problem, and a quantitative determination of a cadmium content in the food, and the like are performed. Hitherto, in the quantitative determination of cadmium, although there have been performed an IPC (induced plasma chromatography) and the like, there have been problems that, in addition to the fact that a time is necessary for such a pretreatment as to make the sample into a solution, a dispersion occurs in a measurement result in dependence on an operator. From the background like this, as a measurement method substituted for the IPC, a fluorescent X-ray analysis is noted. The fluorescent X-ray analysis is one in which a kind and a quantity of an element contained in the sample is specified by irradiating the primary X-ray to the sample and detecting the generated fluorescent X-ray, and hitherto it has been utilized mainly in an analysis of the sample, such as Cu alloy or Fe alloy, whose main component is a heavy element, and the like. Since the fluorescent X-ray has an energy inherent to the element, it is possible to specify the element having been contained in the sample and its quantity by detecting an energy and an intensity of the generated fluorescent X-ray. In the fluorescent X-ray analysis, there suffices if the primary X-ray is directly irradiated to the sample, and there are advantages that a measurement is possible even if the sample is not pretreated and, also as to an analysis result, a reproducibility is good in comparison with the IPC. A detection lower limit denoting an accuracy of the fluorescent X-ray analysis like this is determined by the following expression.

Here, the background intensity means an intensity of an X-ray generated mainly by a scattered ray or the like, which is other than the fluorescent X-ray generated from an aimed element having been contained in the sample, and it becomes a noise of the fluorescent X-ray. Further, the sensitivity is a magnitude of an obtainable X-ray intensity with respect to a concentration of an object element in the fluorescent X-ray analysis apparatus. That is, by decreasing the background intensity and further raising the sensitivity, the detection lower limit decreases, and it becomes possible to realize the quantitative determination of a trace element.

As the fluorescent X-ray analysis apparatus capable of performing the fluorescent X-ray analysis like this, for example, there is proposed one having possessed an X-ray source irradiating the primary X-ray to the sample, a detector detecting the fluorescent X-ray generated from the sample to which the primary X-ray has been irradiated, and a primary filter having plural filter components, or the like (see, e.g., JP-A-2004-150990 Gazette). According to the fluorescent X-ray apparatus like this, by absorbing the primary X-ray of plural energy bands by the primary filter and irradiating the primary X-ray of a necessary energy band, it is possible to decrease the background intensity, thereby improving the detection lower limit.

However, in the fluorescent X-ray analysis apparatus like the above, by causing the primary X-ray to transmit through the primary filter, the primary X-ray itself attenuates. Therefor, since an intensity of the fluorescent X-ray generated from the sample while being excited decreases as well, the intensity of the fluorescent X-ray obtainable by the detector decreases. That is, in the fluorescent X-ray analysis apparatus like the above, while it is possible to decrease the background intensity, the sensitivity decreases. Further, although it is also possible to raise the sensitivity by bringing the X-ray source and the detector close to an irradiation position of the sample, a separation distance between the X-ray source and the detector becomes short as well, so that there has been a limit in a raise of the sensitivity from a spatial limitation. Therefor, there has not led to obtain the detection lower limit capable of precisely measuring a trace aimed element in a light element such as a cadmium content in the food for instance.

This invention is one having been made in view of the above-mentioned circumstances, and one providing a fluorescent X-ray analysis apparatus in which the detection lower limit is improved, and it is possible to quantify the trace aimed element having been contained not only in the sample whose main component is the heavy element but also in the sample whose main component is the light element.

SUMMARY OF THE INVENTION

In order to solve the above problems, this invention proposes the following means.

The present invention is a fluorescent X-ray analysis apparatus quantifying an aimed element contained in a sample, which possesses a sample base supporting the sample, an X-ray source irradiating a primary X-ray to the sample having been supported to the sample base with a predetermined irradiation position being made a center, and a detector disposed toward the irradiation position and detecting a fluorescent X-ray generated from the sample to which the primary X-ray has been irradiated, and is characterized in that the sample base has a detachable sample holding tool fixing the sample while being approached to the X-ray source and the detector, and a measurement is possible by selectively disposing the sample in any one of a 1st inspection position in which an irradiated face to which the primary X-ray is irradiated is coincided with the irradiation position, or a 2nd inspection position in which the sample is fixed to the sample holding tool, the irradiated face to which the primary X-ray is irradiated is approached to the X-ray source, and an inspected face differing from the irradiated face is approached to the detector.

According to the fluorescent X-ray analysis apparatus concerned with this invention, in a case where the sample is one whose main component is the heavy element for instance, the sample is disposed to the 1st inspection position in the sample base. And, by irradiating the primary X-ray by the X-ray source to the irradiated face, of the sample, coinciding with the irradiation position, the sample is excited in an extreme surface range of the sample, in which the irradiation position has been made the center, and the fluorescent X-ray is generated. And, by the fact that the detector is disposed toward the irradiation position, the fluorescent X-ray having been generated is efficiently detected by the detector.

Further, in a case where the sample contains the light element for instance as its main component and the aimed element (element to be quantified) is contained in a trace, the sample is disposed to the 2nd inspection position by mounting the sample holding tool to the sample base and fixing the sample to the sample holding tool. In the 2nd inspection position, the sample is disposed with the irradiated face being approached to the X-ray source. Therefor, since the primary X-ray irradiated from the X-ray source is irradiated, without being attenuated, to the sample in a high density and while having a large solid angle, it is possible to raise an intensity of the primary X-ray irradiated. Further, in a case where the sample contains the light element as its main component, the primary X-ray is transmitted not only through the extreme surface range in which the irradiation position has been made the center like the above but also till an inside of the sample. And, in a range of the sample, to which the X-ray is irradiated and through which it transmits, the primary X-ray excites the aimed element contained in this range, thereby generating the fluorescent X-ray. The fluorescent X-ray having been generated additionally transmits through the inside of the sample, and is detected by the detector. On this occasion, since the detector is disposed while being approached to the inspected face of the sample, and the solid angle to the sample generating the fluorescent X-ray is formed large, the fluorescent X-ray is efficiently entered, without being attenuated, to the detector in a high density, and detected.

Further, it is deemed to be more desirable that, in the above fluorescent X-ray analysis apparatus, the sample base has a window part penetrating from its upper face to its lower face and exposing downward the irradiated face of the sample having been mounted on the upper face as the 1st inspection position, the X-ray source and the detector are disposed below the sample base with a predetermined position of the irradiated face of the sample exposed from the window part being made the irradiation position, and the sample holding tool of the sample base possesses a guide part which opposes the irradiated face of the sample to the X-ray source, slants the sample to a direction opposing the inspected face to the detector, and locks the sample under a state having protruded from an upwardness to a downwardness of the window part.

According to the fluorescent X-ray analysis apparatus concerned with this invention, by mounting the sample to the upper face of the sample base having the window part, it is possible to expose the irradiated face of the sample to the downwardness of the sample base from the window part. In the downwardness of the sample base, the X-ray source and the detector are position-set with a predetermined position of the irradiated face, of the sample, exposing from the window part being made the irradiation position. Therefor, it is possible to detect by the detector the fluorescent X-ray generated from a range, in which the irradiation position has been made the center, by irradiating the primary X-ray to the irradiated face, of the sample, having been exposed with the sample being made the 1st inspection position.

Further, it is possible to dispose the sample while, by the guide part of the sample holding tool, slanting the sample, locking the sample under a state having protruded from the upwardness to the downwardness of the window part, approaching the irradiated face of the sample in a direction opposed to the X-ray source, and approaching the detected face in a direction opposed to the detector. Therefor, it is possible to detect by the detector the fluorescent X-ray generated from the inside of the sample by making the sample into the 2nd inspection position, and irradiating the primary X-ray to and transmitting it through the irradiated face of the sample.

Additionally, it is deemed to be more desirable that, in the above fluorescent X-ray analysis apparatus, the sample holding tool of the sample base is an annular member in which an opening part has been formed, and detachably fitted to the window part while having an engaging part capable of engaging with an outer periphery of the window part, and the guide part is provided while protruding from the opening part so as to be capable of locking the sample having been disposed in the opening part.

According to the fluorescent X-ray analysis apparatus concerned with this invention, in a case where the sample is disposed as the 1st inspection position, it is mounted to the sample base by detaching the sample holding tool from the window part. On the other hand, in a case where the sample is disposed as the 2nd inspection position, the sample holding tool is fitted to the window part by engaging the engaging part of the sample holding tool with the outer periphery of the window part. And, the sample is fixed to the 2nd inspection position by inserting the sample into the opening part of the sample holding tool and being locked by the guide part.

Further, it is deemed to be more desirable that, in the above fluorescent X-ray analysis apparatus, in a position butting against a face opposed to the irradiated face of the sample having been disposed in the 2nd inspection position there is provided a secondary exciting wall having been formed by an element generating a secondary excitation fluorescent X-ray whose energy is higher than an energy of the fluorescent X-ray generated from the aimed element of the sample.

According to the fluorescent X-ray analysis apparatus concerned with this invention, the primary X-ray having been irradiated to the irradiated face, of the sample, having been disposed in the 2nd inspection position transmits through the inside of the sample, excites the aimed element contained in the sample, generates the fluorescent X-ray, and is irradiated to the secondary exciting wall butting against the face opposed to the irradiated face of the sample. The secondary exciting wall generates, by the fact that the primary X-ray is irradiated to it, the secondary excitation fluorescent X-ray whose energy is higher than the energy of the fluorescent X-ray that the aimed element contained in the sample generates. The secondary excitation fluorescent X-ray generated from the secondary exciting wall is irradiated to the sample, and the aimed element of the sample is excited also by the secondary excitation fluorescent X-ray, thereby generating the fluorescent X-ray. Therefor, it is possible to additionally raise an intensity of the fluorescent X-ray generated from the aimed element of the sample, i.e., an intensity of the fluorescent X-ray obtainable by the detector.

Further, it is deemed to be more desirable that, in the above fluorescent X-ray analysis apparatus, there is possessed a sample encapsulation container formed by a material through which the primary X-ray and the fluorescent X-ray can transmit and, in a case where the sample is a solid or a liquid, which has a fluidity, forming the irradiated face and the detected face of the sample while encapsulating in its inside the sample.

According to the fluorescent X-ray analysis apparatus concerned with this invention, also in a case where the sample is the solid or the liquid, which has the fluidity, the sample has a regular shape by being encapsulated in the sample encapsulation container, and it is possible to form the irradiated face and the detected face of the sample. Therefor, similarly to the sample of the solid having a certain regular shape, it is possible to detect the fluorescent X-ray generated from the sample by being disposed in the 1st inspection position or the 2nd inspection position and irradiating the primary X-ray to the sample. Further, even in a case where the sample has been the solid having the regular shape, the sample can be easily made a shape suitable for a measurement by being made a granular form, a powdery form or a liquid by being dissolved, and encapsulated in the sample encapsulation container. Incidentally, since the sample encapsulation container is formed by the material through which the primary X-ray and the fluorescent X-ray can transmit, there is no fact that the primary X-ray and the fluorescent X-ray attenuate and the intensity of the fluorescent X-ray obtainable by the detector decreases.

Additionally, it is deemed to be more desirable that, in the above fluorescent X-ray analysis apparatus, the sample encapsulation container is formed in a trapezoidal shape in section, which has an upper face forming the detected face of the sample, and a side face forming the irradiated face of the sample.

According to the fluorescent X-ray analysis apparatus concerned with this invention, by the fact that the sample encapsulation container is formed in the trapezoidal shape in section, the sample encapsulated in the sample encapsulation container and having been fixed to the 2nd inspection position is disposed radiately with respect to the detector. Therefor, if an angle opening from an upper side to a lower side of the trapezoid that is the sectional shape of the sample encapsulation container is set to an angle equal to a detectable solid angle of the detector, it is possible to efficiently detect the fluorescent X-ray generated from the whole sample having been encapsulated.

According to the fluorescent X-ray analysis apparatus of the present invention, by possessing the X-ray source irradiating the primary X-ray with the predetermined irradiation position being made the center and the detector having been disposed toward the irradiation position, in the case where the sample contains the heavy element as its main component, it is possible to detect the fluorescent X-ray generated from the range in which the irradiation position is made the center by disposing the sample to the 1 st inspection position. Further, by mounting the sample holding tool to the sample base, it is possible to dispose the sample while being approached to the X-ray source and the detector with the sample being made the 2nd inspection position. Therefor, it is possible to raise the intensity, i.e., sensitivity, of the fluorescent X-ray obtainable by the detector to thereby improve the detection lower limit, and it is possible to realize an accurate quantitative determination of the trace aimed element having been contained not only in the sample whose main component is the heavy element but also in the sample whose main component is the light element.

BRIEF DESCRIPTION OF THE DRAWINGS

FIG. 7 is a perspective view of a sample encapsulation container of the embodiment of this invention.

DETAILED DESCRIPTION OF THE INVENTION

Figure 1:
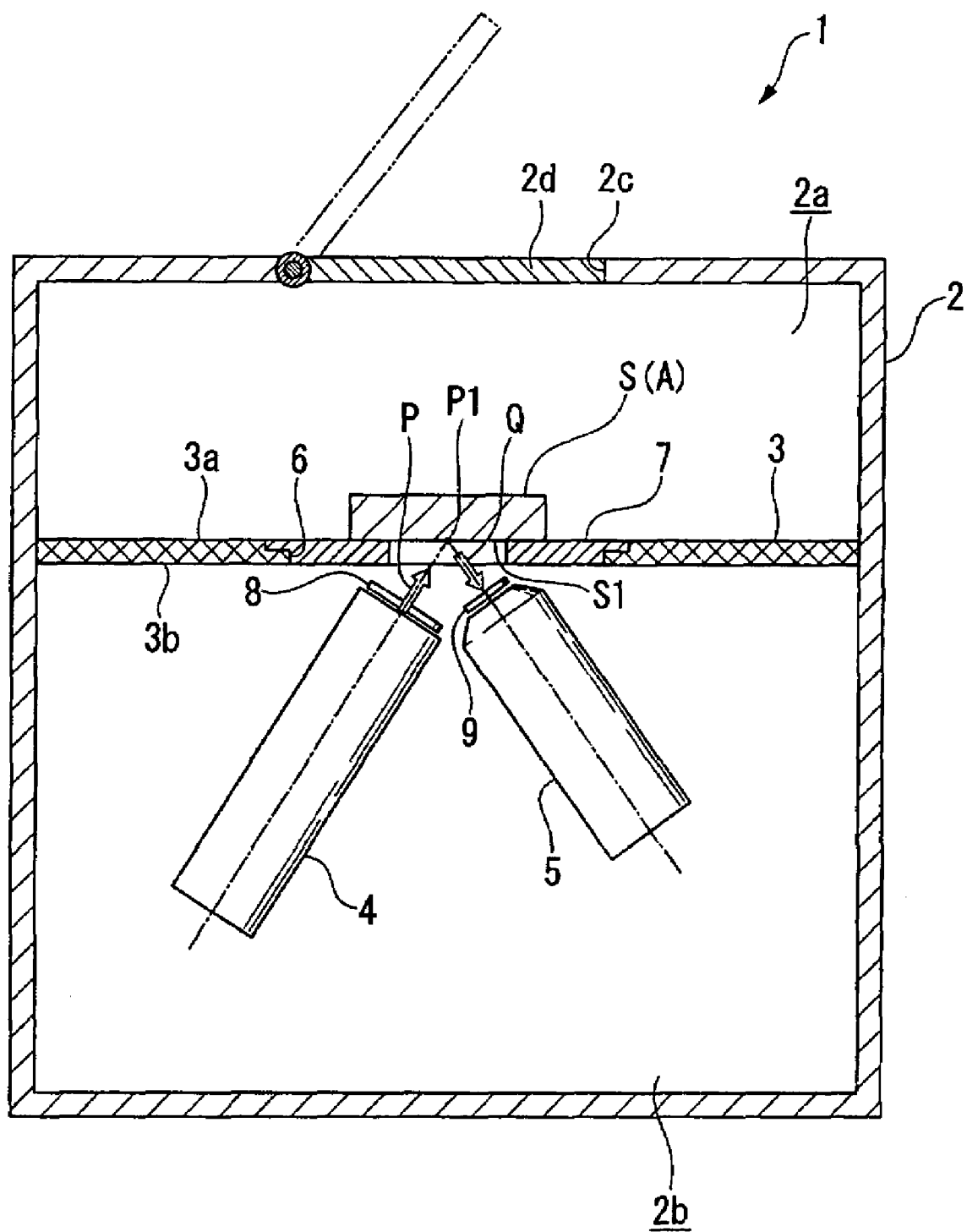
FIG. 1 is a sectional view showing a schema of a fluorescent X-ray analysis apparatus of an embodiment of this invention.
Figure 2:
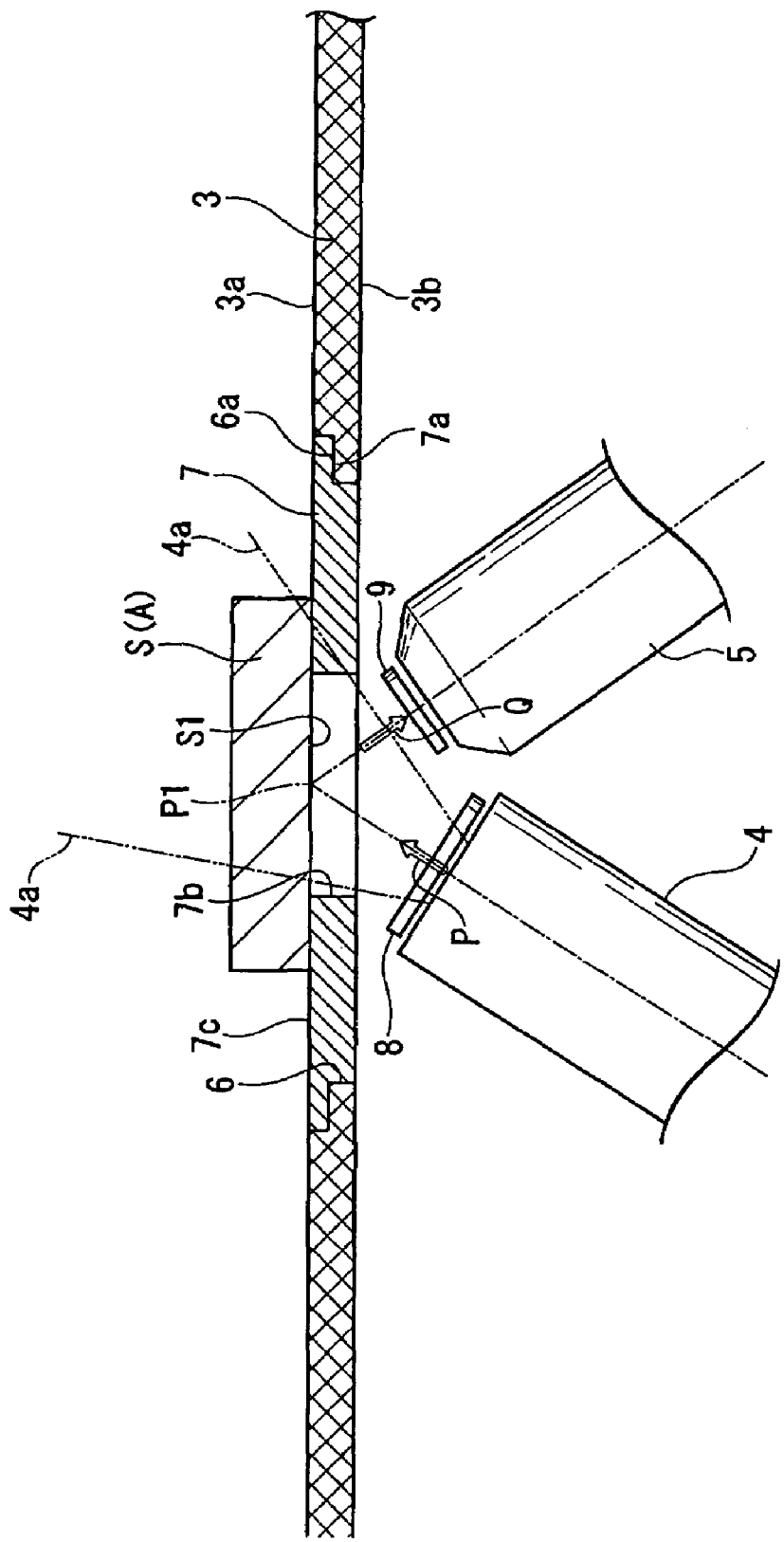
FIG. 2 is an enlarged sectional view of the fluorescent X-ray analysis apparatus of the embodiment of this invention.
Figure 3:
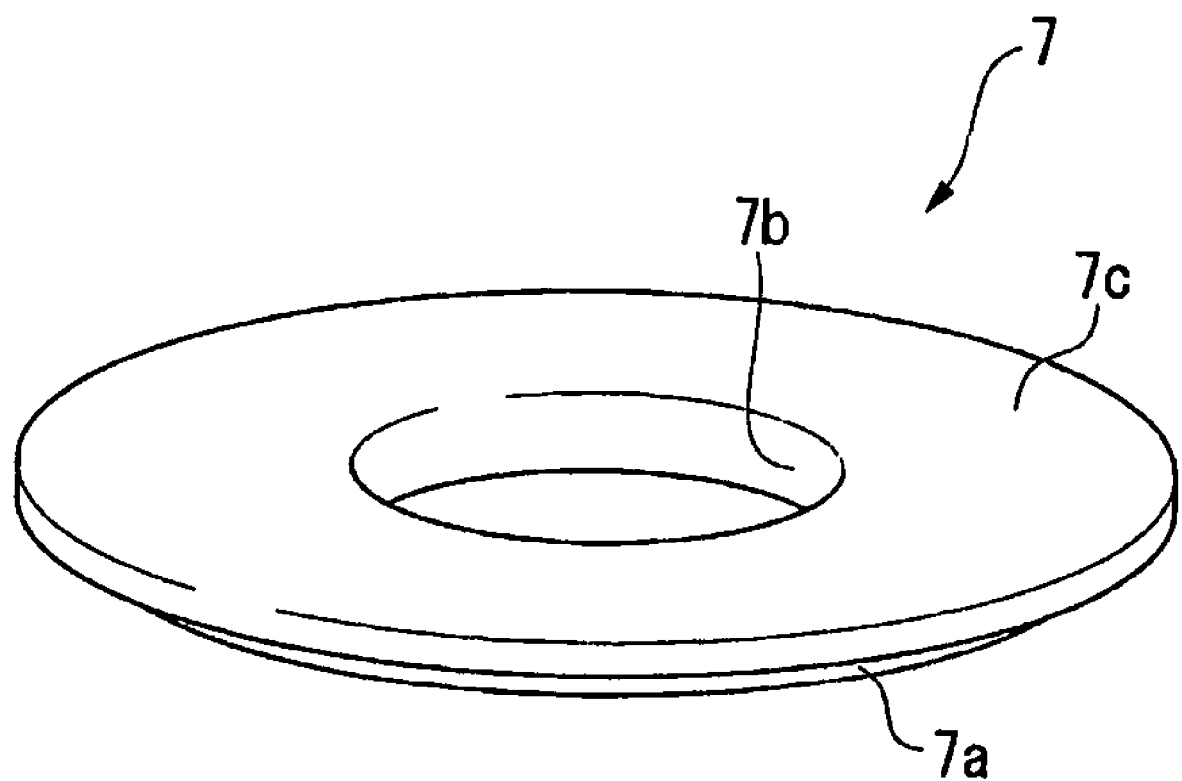
FIG. 3 is a perspective view of an auxiliary tool of the embodiment of this invention.

FIG. 1 to FIG. 4 show an embodiment concerned with this invention. As shown in FIG. 1, a fluorescent X-ray analysis apparatus 1 possesses an outer casing 2, a sample base 3 supporting a sample S, an X-ray source 4 irradiating a primary X-ray P to the sample S, and a detector 5 detecting a fluorescent X-ray Q generated from the sample S. The sample base 3 is provided in an inside of the outer casing 2, and the inside of the outer casing 2 is partitioned to a sample chamber 2a above the sample base 3, and a measurement chamber 2b in which the X-ray source 4 and the detector 5 have been disposed. In an upper part of the sample chamber 2a, an opening part 2c is formed, and a sample chamber upper lid 2d is provided so as to be openable/closable. As shown in FIG. 2, the sample base 3 has a window part 6 penetrating from an upper face 3a to a lower face 3b. And, the sample base 3 can mount the sample S to the upper face 3a as a 1st inspection position A under a state in which an irradiated face S1 of the sample S has been exposed downward from the window part 6. Incidentally, in the present embodiment, a step part 6a is formed in an outer periphery of the window part 6, and there is detachably fitted an auxiliary tool 7 in which an engaging part 7a capable of engaging with the step part 6a has been formed. As shown in FIG. 2 and FIG. 3, an opening part 7b is formed in the auxiliary tool 7. Further, there is set such that, when having been fitted to the window part 6, an upper face 7c of the auxiliary tool 7 coincides with the upper face 3a of the sample base 3. Therefor, even in a case where the sample S is small, by fitting the auxiliary tool 7 to the window part 6, it is possible to dispose the sample S to the 1st inspection position A. Incidentally, in a case where the sample S is sufficiently larger than the window part 6, it may be directly mounted to the sample base 3 without fitting the auxiliary tool 7.

As shown in FIG. 1, the X-ray source 4 is an X-ray tube bulb for instance, and one irradiating the primary X-ray P having been constituted by a characteristic X-ray and a continuous X-ray of a target of the X-ray tube bulb. In a case where the sample S has been disposed on the sample base 3 as the 1st inspection position A, the X-ray source 4 is disposed below the sample base 3 so as to irradiate with an irradiation position P1 coinciding with the irradiated face S1 of the sample S, which is exposed downward from the window part 6, being made a center. Below the sample base 3, the detector 5 is disposed toward the irradiation position P1, and can detect an energy and an intensity of the fluorescent X-ray generated from the sample S. Further, the detector 5 is disposed outside an irradiation range 4a of the X-ray source 4, and set such that the primary X-ray P is directly irradiated.

Further, in front of the X-ray source 4 and the detector 5, there are provided respectively a primary filter 8 and a secondary filter 9. The primary filter 8 is one absorbing only an X-ray of a specified energy within the primary X-ray P irradiated from the X-ray source 4. And, by absorbing an X-ray of the same energy range as the fluorescent X-ray generated from the aimed element having been contained in the sample S, it is possible to prevent the detection lower limit from rising due to the fact that a scattered ray and the like are detected by the detector and the background intensity rises. For example, if it is supposed that the aimed element is Cd, by forming the primary filter 8 by Mo or Zr, it is possible to absorb the primary X-ray of the same energy range as the fluorescent X-ray of Cd, thereby decreasing the background intensity and improving the detection lower limit. Incidentally, in the present embodiment, there is made so as to be capable of being switched to the primary filters of various kinds by a moving mechanism not shown in the drawing while corresponding to the aimed element.

Further, similarly, the secondary filter 9 is also one absorbing only the X-ray of the specified energy within the X-ray detected. And, by absorbing an X-ray whose energy range differs from the fluorescent X-ray generated from the aimed element having been contained in the sample S, the detector 5 can detect the fluorescent X-ray of the specified energy, and it is possible to suppress the X-ray intensity of the whole, thereby raising a detection efficiency. For example, if it is supposed that the aimed element is Cd, by forming the secondary filter 9 by Ag or the like, it is possible to absorb an X-ray whose energy is higher than the fluorescent X-ray of Cd, thereby suppressing the X-ray intensity of the whole. Incidentally, in the present embodiment, there is made so as to be capable of being switched to the secondary filters of various kinds by a moving mechanism not shown in the drawing while corresponding to the aimed element.

Incidentally, the fluorescent X-ray analysis apparatus 1 of the present embodiment possesses additionally, although not shown in the drawing, a control section, a computer section, an amplifier, a waveform shaper, a monitor, and the like. The control section performs a control of the primary X-ray P irradiated from the X-ray source 4, and further performs selections of the primary filter 8 and the secondary filter 9. Further, a detection result having been detected by the detector 5 is amplified by the amplifier, and converted to an electric signal by the waveform shaper. Additionally, there is made a constitution in which the detection result having been converted to the electric signal is converted by the computer section to an intensity spectrum for every energy and displayed to the monitor.

Figure 4:
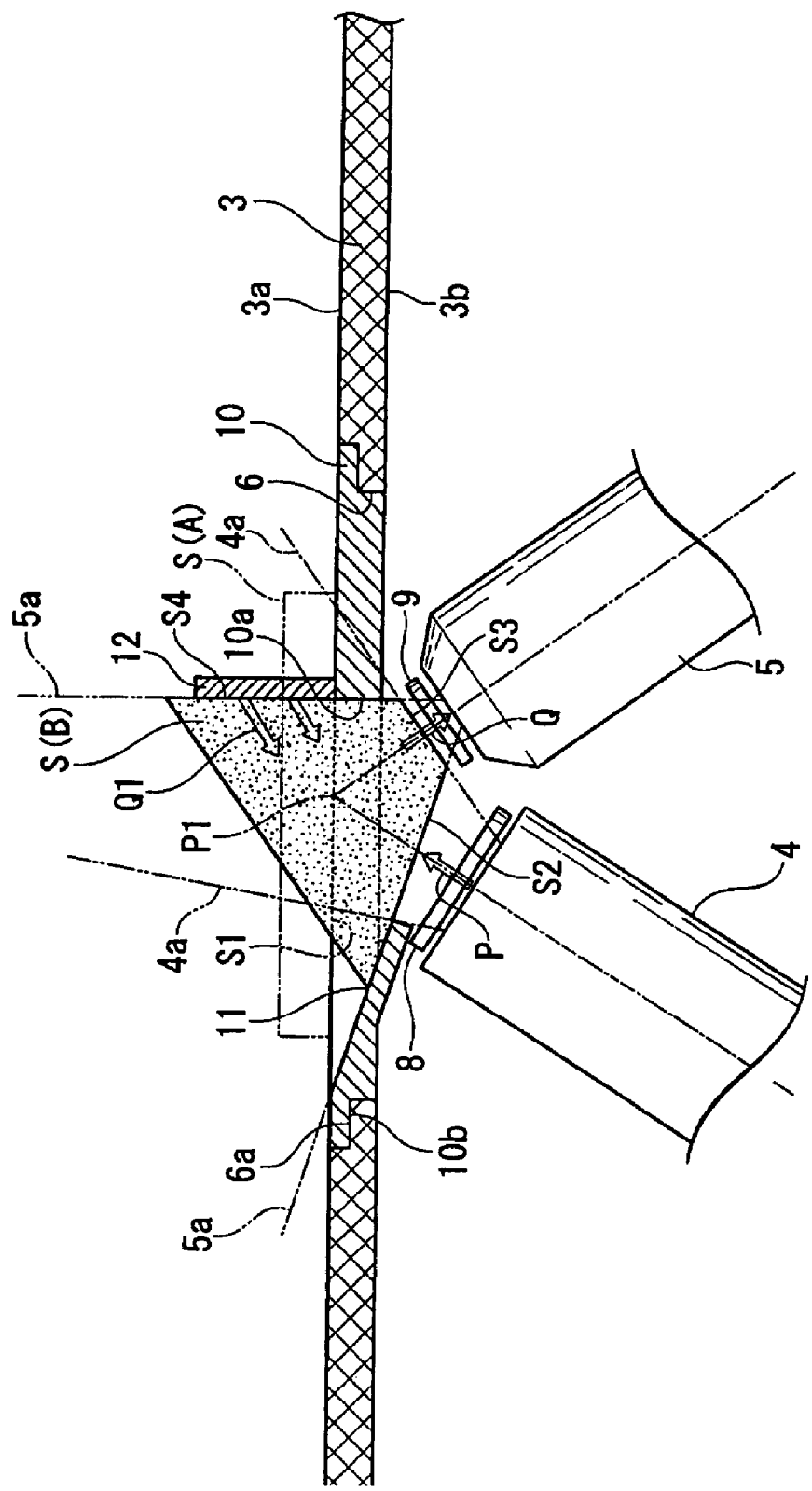
FIG. 4 is an enlarged sectional view of the fluorescent X-ray analysis apparatus of the embodiment of this invention.
Figure 5:
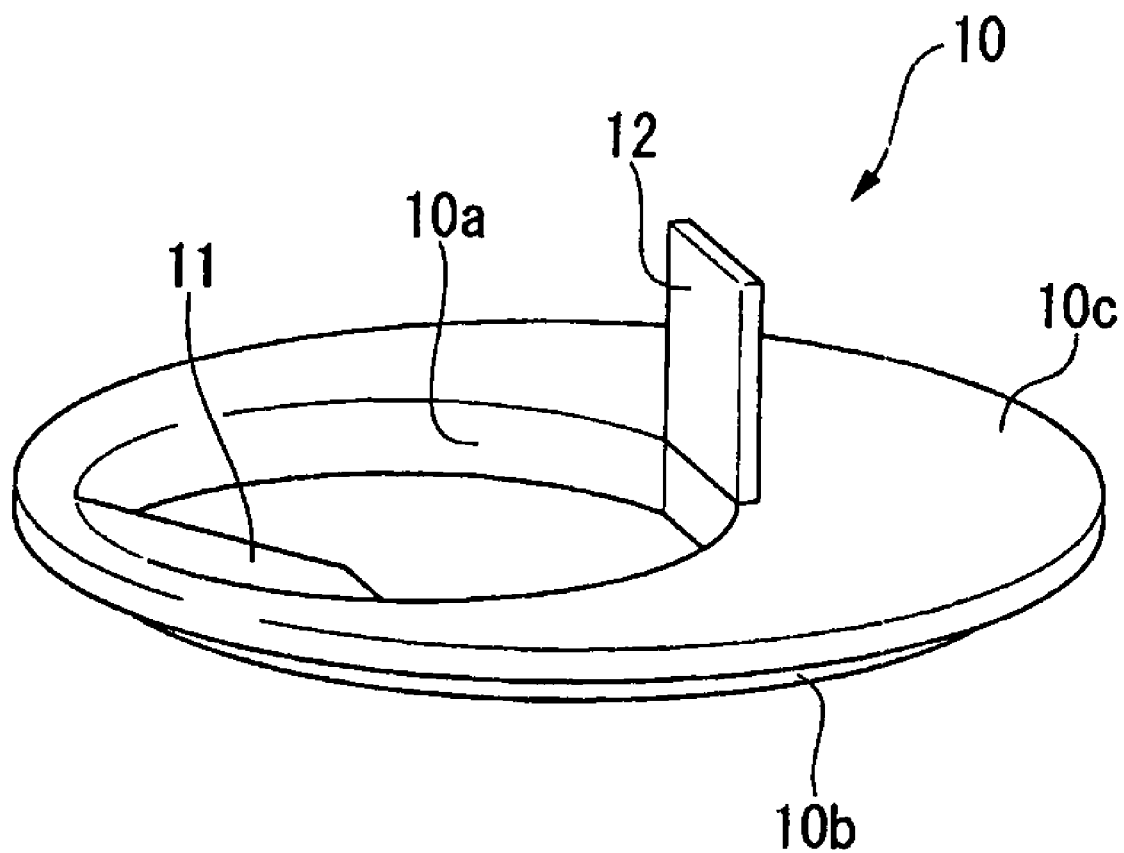
FIG. 5 is a perspective view of a sample holding tool of the embodiment of this invention.

Further, as shown in FIG. 4 and FIG. 5, the sample base 3 can fit a sample holding tool 10 to the window part 6 instead of the auxiliary tool 7. The sample holding tool 10 is an annular member in which an opening part 10a has been formed, which has an engaging part 10b capable of engaging with the step part 6a of the window part 6, and can be detachably fitted. Further, a guide part 11 is provided while protruding to the opening part 10a under a state having been slanted downward toward a center part of the opening part 10a. And, the sample S having been inserted into the opening part 10a is locked under a state protruding from an upwardness to a downwardness of the window part 6, an irradiated face S2 of the sample S having been locked by the guide part 11 is approached to the X-ray source 4 in a direction opposed thereto, and the sample S is fixed to a 2nd inspection position B in which an inspected face S3 is approached to the detector 5 in a direction opposed thereto. Further, a position and a shape of the guide part 11 and a shape of the sample S are set such that the inspected face S3 of the sample S is disposed in a position approximately equal to a boundary line of the irradiation range 4a of the primary X-ray P of the X-ray source 4, and the irradiated face S2 is disposed in a position approximately equal to a boundary line of a detection range 5a of the detector 5, respectively. Incidentally, there may be made a constitution in which the step part 6a is not formed in the outer periphery of the window part 6, and the sample holding tool 10 is directly engaged with the outer periphery of the window part 6.

Additionally, in an upper face 10c of the sample holding tool 10, in a position butting against a face S4 opposed to the irradiated face S2 of the sample S having been disposed in the 2nd inspection position B, there is provided a secondary exciting wall 12. The secondary exciting wall 12 is formed by a material generating a secondary fluorescent X-ray Q1 whose energy is higher than an energy of a fluorescent X-ray Q generated from the aimed element of the sample S and, in a case where the aimed element is Cd for instance as mentioned later, it is formed by Te and the like. Incidentally, the secondary exciting wall 12 may be made exchangeable with one of various materials while corresponding to the aimed element by being made a constitution detachable from the sample holding tool 10 by a screw fixation and the like, or may be made one fixed, e.g., to the sample base 3 other than the sample holding tool 10.

Figure 6:
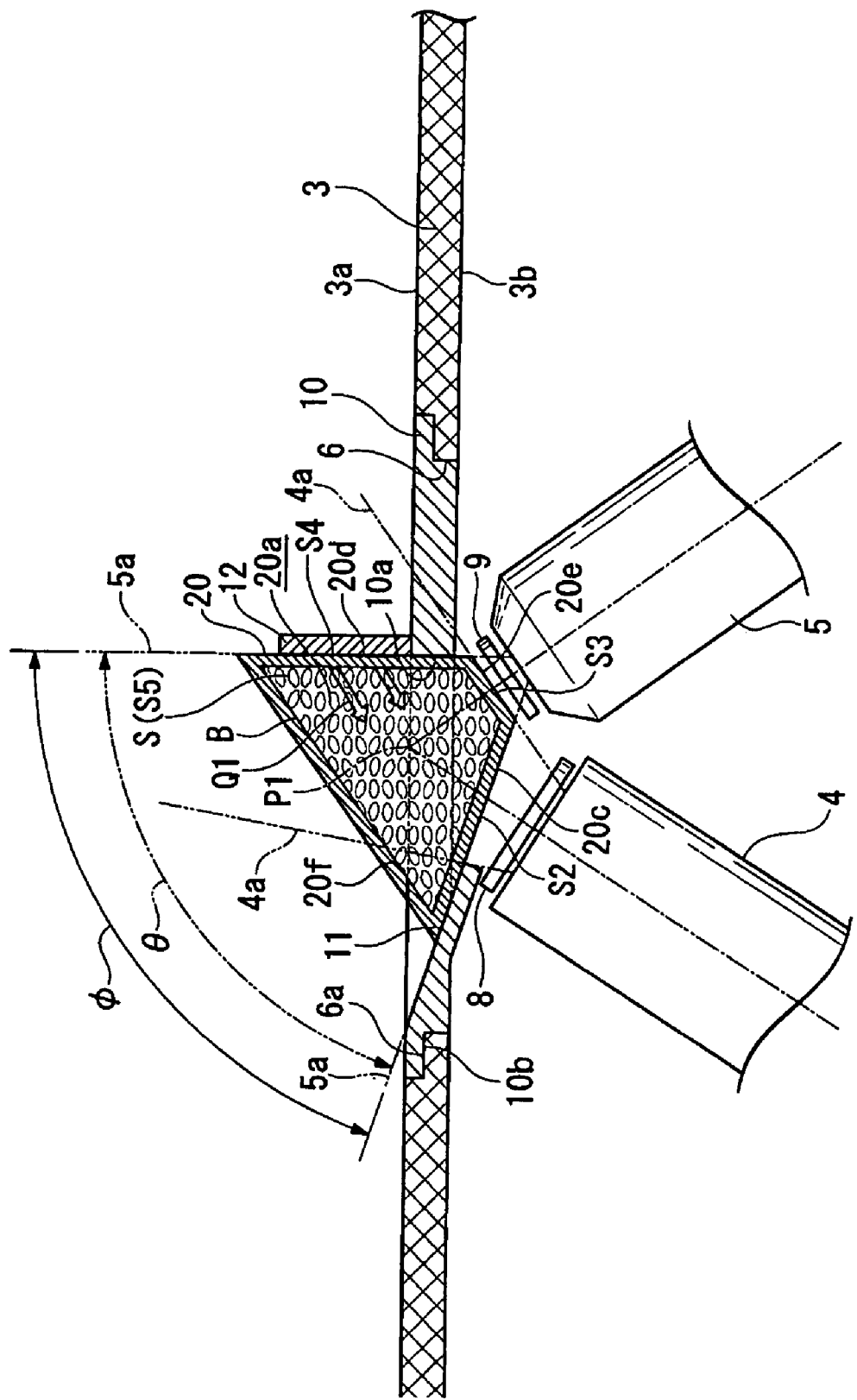
FIG. 6 is an enlarged sectional view of the fluorescent X-ray analysis apparatus of the embodiment of this invention.

Further, as shown in FIG. 6 and FIG. 7, in a case where the sample S is a solid or a liquid, which has a fluidity, the fluorescent X-ray analysis apparatus 1 possesses a sample encapsulation container 20 encapsulating the sample S in an inside 20a. The sample encapsulation container 20 is formed by a material through which the X-ray including the primary X-ray P and the fluorescent X-ray Q can transmit, and formed by plastic, Al, Si or Mg and the like for instance. Further, as the sample S, for example, as the solid having the fluidity, there is granular one such as rice, beans or soil, or a powdery one, such as flour, or the like and, also as to a solid article having a certain regular shape, there is included also one becoming granular or powdery by a working. Further, as the liquid, there is included also one in which the sample that is the solid has been dissolved. In the present embodiment, the rice is enumerated as a sample S5 having the fluidity. The sample encapsulation container 20 is provided with an openable/closable lid 20b, and makes it possible to encapsulate the sample S5 to the inside 20a. Further, the encapsulation container 20 is formed in a trapezoidal shape in section, which has, in the 2nd inspection position B, a side face 20c forming the irradiated face S2, of the sample S, approaching to the X-ray source 4, a side face 20d butting against the secondary exciting wall 12, and an upper face 20e forming the inspected face S3, of the sample S, approaching to the detector 5. And, an angle Φ which opens from an upper side (the upper face 20e) to a lower side (a lower face 20f) of the trapezoid that is a sectional shape is set so as to be approximately equal to a solid angle θ denoting the detection rage 5a of the detector 5.

Next, there is explained about actions of this fluorescent X-ray analysis apparatus 1. First, there is explained about a measurement in a case where the sample S is, e.g., a Cu alloy, an Fe alloy or the like, whose main component is the heavy element. As shown in FIG. 2, in a case where there is measured the sample S whose main component is the heavy element, the auxiliary tool 7 is fitted to the sample base 3, and the sample is disposed by selecting the 1st inspection position A. And, if the primary X-ray P is irradiated from the X-ray source 4, it passes through the primary filter 8, and the primary X-ray P is irradiated to the sample S with the irradiation position P1 coinciding with the irradiated face S1 of the sample S being made a center. Since the sample S contains the heavy element as its main component, the primary X-ray P is not transmitted till the inside of the sample S, and the sample S is excited in an extreme surface range in which the irradiation position P1 of the irradiated face S1 of the sample S has been made the center, thereby generating the fluorescent X-ray Q. The fluorescent X-ray Q having been generated passes through the secondary filter 9, and is detected by the detector 5. On this occasion, since the detector 5 is disposed toward the irradiation position P1, it is possible to efficiently detect the fluorescent X-ray Q having been generated.

Next, there is explained about a measurement in a case where the sample S contains the light element as its main component and the aimed element (element to be quantified) is contained in a trace. First, there is explained about a case where the sample S has the certain regular shape. Incidentally, the light element means an element through which the primary X-ray P can transmit and, the smaller an atomic number of the element is, the higher becomes an transmittance of the X-ray, and it is C, H, O or Al, Mg and the like, and one including also an organic material and the like. Further, as the aimed element, there suffices if it is an element generating the fluorescent X-ray whose energy is larger than the element constituting at least the main component, and there correspond various ones from the above light elements to the heavy elements. Incidentally, in the present embodiment, there is explained about a case where Cd is quantified as the aimed element.

First, as shown in FIG. 4, the sample holding tool 10 is fitted to the window part 6 of the sample base 3. Next, the sample S is inserted from above to the opening part 10a of the sample holding tool 10, and the sample S is fixed to the 2nd inspection position B by the guide part 11. In the 2nd inspection position B, the sample S is slanted by the guide part 11, and locked under a state having protruded from an upwardness to a downwardness of the opening part 10a, and the irradiated face S2 of the sample S becomes a state having faced on and approached to the X-ray source 4. Further, the detected face S3 of the sample S is set to the position approximately equal to the boundary line of the irradiation rage 4a. Therefor, the primary X-ray P having been irradiated from the X-ray source 4 passes through the primary filter 8, and is irradiated to the whole of the sample S without being attenuated and while having a high density and a large solid angle. Additionally, by the fact that the sample S is disposed such that the detected face S3 becomes the position approximately equal to the boundary line of the irradiation range 4a of the primary X-ray P, the primary X-ray P is more efficiently irradiated to the whole of the sample S. By the fact that the sample S contains the light element as its main component, the primary X-ray P having been irradiated to the sample S is transmitted till the inside of the sample S, and the aimed element contained in the whole inside of the sample S is excited, thereby generating the fluorescent X-ray.

Additionally, the primary X-ray P transmits through the sample S, and is irradiated to the secondary exciting wall 12 butting against the face S4 opposed to the irradiated face S2 of the sample S. By being irradiated, the secondary exciting wall 12 is excited, thereby generating the secondary excitation fluorescent X-ray Q1 whose energy is higher than the energy of the fluorescent X-ray Q generated from the aimed element contained in the sample S. From the fact that the secondary excitation fluorescent X-ray Q1 having been generated is irradiated to the sample S and has a higher energy than the energy of the fluorescent X-ray Q generated from the aimed element, the aimed element contained in the whole inside of the sample S is excited again, thereby generating the fluorescent X-ray Q. That is, by having the secondary exciting wall 12, the sample S is excited not only by the primary X-ray P but also by the secondary excitation fluorescent X-ray Q1, so that the intensity of the fluorescent X-ray Q generated is raised. And, the fluorescent X-ray Q having been generated by the primary X-ray P and the secondary excitation fluorescent X-ray Q1 transmits through the inside of the sample S, passes through the secondary filter 9, and is detected by the detector 5. In the second inspection position B, the inspected face S3 of the sample S is disposed while approaching to the detector 5, and the solid angle to the sample is formed large. Therefor, the fluorescent X-ray Q is efficiently entered to the detector 5 without being attenuated and at a high density, and detected.

Next, there is explained about a case where the sample S is the fluidic solid or liquid. In this embodiment, there is explained about a case where there is quantified with Cd, which is contained in the rice that is the granular sample S5 having the fluidity, being made the aimed element. First, as shown in FIG. 6, the sample S is encapsulated to the sample encapsulation container 20. Next, the side face 20c is approached to the X-ray source 4, and the upper face 20e is approached to the detector 5, thereby fixing the sample S to the inspection position B. Under this state, if the primary X-ray P is irradiated from the X-ray source 4, the primary X-ray P passes through the primary filter 8, transmits through the sample encapsulation container 20, and is irradiated to the sample S having been encapsulated, thereby exciting the aimed element Cd contained and generating the fluorescent X-ray Q. On this occasion, additionally, the primary X-ray P transmits through the sample S, and is irradiated to the secondary exciting wall 12, thereby generating the secondary excitation fluorescent X-ray Q1 from the secondary exciting wall 12. Since the secondary excitation fluorescent X-ray Q1 is irradiated to the sample S, excites the aimed element Cd again, and generates the fluorescent X-ray Q, the intensity of the fluorescent X-ray Q is raised.

The fluorescent X-ray Q having been generated transmits through the inside of the sample S and the sample encapsulation container 20, passes through the secondary filter 9 from the upper face 20e, and is detected by the detector 5. On this occasion, similarly to the above, in the 2nd inspection position B, the inspected face S3 of the sample S is disposed while approaching to the detector 5, and the solid angle to the sample is formed large. Therefor, the fluorescent X-ray Q is efficiently entered to the detector 5 without being attenuated and at the high density, and detected. Further, since the angle Φ of the sample encapsulation container 20 is set so as to be approximately equal to the solid angle θ of the detector 5, which can be detected, with a minimum sample, the detection can be efficiently performed in a whole region capable of being detected.

Like the above, in the fluorescent X-ray analysis apparatus 1 of this embodiment, there are possessed the X-ray source 4 irradiating the primary X-ray P with the predetermined irradiation position P1 being made the center, and the detector 5 having been disposed toward the irradiation position P1. Therefor, in the case where the sample S contains the heavy element as its main component, it is possible to dispose the sample S while selecting the 1st inspection position A, thereby efficiently detecting the fluorescent X-ray Q generated from a range in which the irradiation position P1 has been made the center. Further, by fitting the sample holding tool 10 to the sample base 3, it is possible to select the 2nd inspection position B, thereby disposing the sample S while being approached to the X-ray source 4 and the detector 5. Therefor, it is possible to raise the intensity, i.e., the sensitivity, of the fluorescent X-ray Q obtainable by the detector 5 to thereby improve the detection lower limit, so that it is possible to realize an accurate quantitative determination of the trace aimed element having been contained not only in the sample whose main component is such a heavy element as mentioned above but also in the sample whose main component is the light element. Additionally, by possessing the sample encapsulation container 20, also in the case where the sample S is formed by the solid or the liquid, which has the fluidity, it is possible to realize the accurate quantitative determination of the trace aimed element. Therefor, in the cadmium pollution of the food, which is noted in the recent years, or the like, a trace cadmium content in the food, or the like can be quantified, and it can be measured irrespective of a form of the food becoming the sample.

In the above, although there has been detailedly mentioned about the embodiment of the present invention by referring to the drawings, a concrete constitution is not one limited to this embodiment, and there is included also a design modification or the like in a scope not deviating from a gist of the present invention.

Incidentally, in the present embodiment, although the sample holding tool 10 has been made one which is an annular member and fitted to the window part 6, there is not limited to this. There suffices if it is one capable of fixing the sample S at least as the 2nd inspection position B, and there may be made a constitution in which only the guide part 11 is directly fixed to the sample base 3. Further, in the 2nd inspection position B, although the irradiated face S2 of the sample S is disposed while approaching to the X-ray source 4, there suffices if the irradiated face S2 is disposed in a position having approached than at least the irradiation position P1 and, by approaching the irradiated face S2 in a range not interfering with the X-ray source 4 or the primary filter 8, it is possible to expect a larger effect. Similarly, there suffices if the inspected face S3 of the sample S is disposed while approaching to the detector 5 than at least the irradiation position P1 and, by approaching the inspected face S3 in a range not interfering with the detector 5 or the secondary filter 9, it is possible to expect the larger effect.

Further, although the fluorescent X-ray analysis apparatus 1 is made basically a constitution in which the sample base 3 has the window part 6 and is placed in the upwardness, and the sample S exposed from the window part 6 is measured by the X-ray source 4 and the detector 5, which have been placed in the downwardness, there is not limited to this. For example, there may be made a constitution in which the X-ray source 4 and the detector 5 are disposed in a side with respect to the sample S having been disposed on the sample base 3 with a predetermined position of the sample base 3 being made the 1st inspection position A, thereby performing the measurement with a side face of the sample S being made the above irradiated face S1. In this case, there suffices if it is one in which the sample holding tool 10 is provided on the sample base 3, the irradiated face S2 of the sample S is approached to the X-ray source 4, and the sample S is positioned in a position (the 2nd inspection position B) in which the inspected face S3 has been approached to the detector 5. Further, as to the primary filter 8, the secondary filter 9 and the secondary exciting wall 12, they are ones suitably provided and, even if they are not provided, it is possible by the above constitution to raise the sensitivity detected by the detector and improve the detection lower limit.

What is claimed is:

1. A fluorescent X-ray analysis apparatus quantifying an aimed element contained in a sample, which possesses:
    a sample base stationarily supporting the sample,
    an X-ray source directed to a predetermined irradiation point and irradiating a primary X-ray to an irradiation face of the sample supported by the sample base at the predetermined irradiation point,
    a detector directed toward the predetermined irradiation point and detecting a fluorescent X-ray generated from an inspection face of the sample to which the primary X-ray has been irradiated, and
    sample holding tools differently configured such that the sample holding tools are selectively set in the sample base to stationarily support the sample at the predetermined irradiation point respectively in a 1st inspection position and in a 2nd inspection position based on a type of the sample, wherein:
    the 1st inspection position is a position in which the irradiation face and the inspection face at least partially overlap each other in a single surface of the sample, and
    the 2nd inspection position is a position in which the irradiation face and the inspection face reside in different surfaces of the sample.

2. The fluorescent X-ray analysis apparatus according to claim 1, further comprising a secondary excitation wall being in contact with a face of the sample opposed to the irradiation face of the sample when the sample is positioned in the 2nd inspection position, wherein the secondary excitation wall made of a material which generates a secondary excitation fluorescent X-ray whose energy is higher than an energy of the fluorescent X-ray generated from the sample.

3. The fluorescent X-ray analysis apparatus according to claim 1, wherein the sample is contained in a sample encapsulation container made of a material through which the primary X-ray and the fluorescent X-ray can transmit.

4. The fluorescent X-ray analysis apparatus according to claim 3, wherein the sample encapsulation container is formed in a trapezoidal shape in cross-section, which has a top face forming the inspection face of the sample, and a side face forming the irradiation face of the sample.

5. The fluorescent X-ray analysis apparatus according to claim 1, wherein the sample base has a window part penetrating from its upper face to its lower face and exposing downward the irradiated face of the sample having been mounted on the upper face as the 1st inspection position.

6. The fluorescent X-ray analysis apparatus according to claim 5, wherein the X-ray source and the detector are disposed below the sample base with a predetermined position of the irradiated face of the sample exposed from the window part being made the irradiated position.

7. The fluorescent X-ray analysis apparatus according to claim 6, wherein one of the sample holding tools of the sample base has possessed a guide part which opposes the irradiated face of the sample to the X-ray source, slants the sample to a direction opposing the inspected face to the detector, and locks the sample under a state having protruded from an upwardness to a downwardness of the window part.

8. The fluorescent X-ray analysis apparatus according to claim 7, wherein:
    the one sample holding tool of the sample base is an annular member in which an opening part has been formed, and detachably fitted to the window part while having an engaging part capable of engaging with an outer periphery of the window part, and
    the guide part is provided while protruding from the opening part so as to be capable of locking the sample having been disposed in the opening part.

9. A fluorescent X-ray analysis apparatus for analyzing elements contained in a sample, comprising:
    a primary axis and a secondary axis which intersect each other at an inspection point at an intersecting angle formed therebetween;
    an X-ray source configured to irradiate a primary X-ray along the primary axis onto the sample;
    a detector directed along the secondary axis to detect a fluorescent X-ray excited out from the sample along the secondary axis;
    a base configured to hold the sample at the inspection point, wherein the X-ray source, the detector and the base are geometrically stationary relative to each other; and
    sample holders differently configured such that the sample holders are selectively set in the base to stationarily position the sample at the inspection point respectively in a 1st position and a 2nd position according to a type of the sample, wherein the inspection point is situated at or nearly at a surface of the sample positioned in the 1st position, whereas the inspection point is situated relatively deep inside the sample positioned in the 2nd position.

10. The fluorescent X-ray analysis apparatus according to claim 9, wherein the intersecting angle is defined such that the X-ray source does not irradiate the primary X-ray directly onto the detector.

11. The fluorescent X-ray analysis apparatus according to claim 9, wherein the detector has a detection bound defining a frustoconical space, and the sample is shaped and positioned in the 2nd position such that it substantially fits in the frustoconical space.

* * * * *